(12) United States Patent  
Nakakado

(10) Patent No.: US 8,440,039 B2  
(45) Date of Patent: May 14, 2013

(54) METHOD FOR MANUFACTURING DISPOSABLE WORN ARTICLE

(75) Inventor: Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 59 days.

(21) Appl. No.: 13/148,334

(22) PCT Filed: Feb. 9, 2010

(86) PCT No.: PCT/JP2010/051837  
§ 371 (c)(1),  
(2), (4) Date: Aug. 8, 2011

(87) PCT Pub. No.: WO2010/092935  
PCT Pub. Date: Aug. 19, 2010

(65) Prior Publication Data  
US 2011/0303351 A1    Dec. 15, 2011

(30) Foreign Application Priority Data

Feb. 12, 2009   (JP) ................................ 2009-029307

(51) Int. Cl.  
*A61F 13/49* (2006.01)

(52) U.S. Cl.  
USPC ........................... 156/204; 156/226; 493/405

(58) Field of Classification Search ................... None  
See application file for complete search history.

(56) References Cited

U.S. PATENT DOCUMENTS

| | | | |
|---|---|---|---|
| 5,855,574 A | 1/1999 | Kling et al. | |
| 6,513,221 B2 * | 2/2003 | Vogt et al. | 29/429 |
| 2003/0135190 A1 | 7/2003 | Widlunc et al. | |
| 2004/0129592 A1 * | 7/2004 | Otsubo | 206/440 |
| 2008/0009816 A1 | 1/2008 | Kenmochi et al. | |
| 2008/0208152 A1 * | 8/2008 | Eckstein et al. | 604/365 |
| 2008/0255534 A1 * | 10/2008 | Reyes | 604/391 |
| 2011/0100526 A1 * | 5/2011 | Umebayashi | 156/66 |

FOREIGN PATENT DOCUMENTS

JP    2002-518097 A    6/2002

(Continued)

OTHER PUBLICATIONS

International Search Report for corresponding International Application No. PCT/JP2010/051837 mailed Apr. 20, 2010.

*Primary Examiner* — Barbara J Musser  
(74) *Attorney, Agent, or Firm* — Renner, Otto, Boisselle & Sklar, LLP

(57) ABSTRACT

It includes: a carrying step of carrying a continuous member of a combined web in a direction perpendicular to a girth direction Y; a first folding step of folding a girth portion 3, while performing the carrying step, so that a non-skin-contact surface 3b of the girth portion 3 lies on a non-skin-contact surface 3b of one of first and second side flaps; a second folding step of folding the first and second side flaps, while performing the carrying step and after the first folding step, so that skin-contact surfaces 3a of the first and second side flaps lie on skin-contact surfaces 3a of a back portion and a front portion; a cut-off step of cutting the continuous member into individual worn articles, after the second folding step; and a third folding step of folding the individual worn articles so that a first fastener member 31 provided on a skin-contact surface 3a of the girth portion 3 lies on a second fastener member 32 provided on a non-skin-contact surface 3b of the other one of the first and second side flaps.

5 Claims, 10 Drawing Sheets

| | FOREIGN PATENT DOCUMENTS | | |
|---|---|---|---|
| JP | 2006-150068 A | 6/2006 | |
| JP | 2006-175007 A | 7/2006 | |

| | | | |
|---|---|---|---|
| WO | 99/65441 | A1 | 12/1999 |
| WO | 02/065961 | A2 | 8/2002 |

* cited by examiner

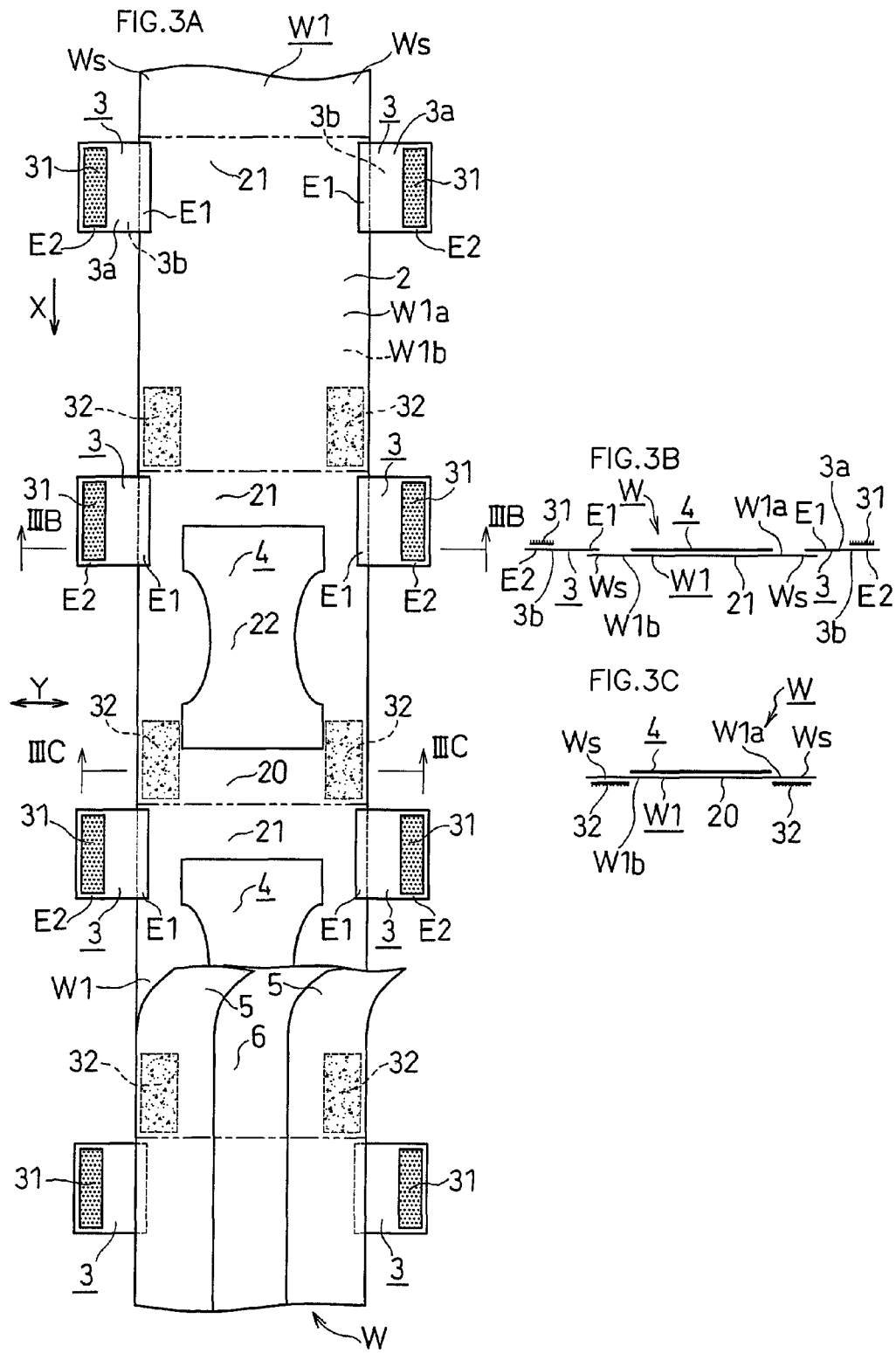

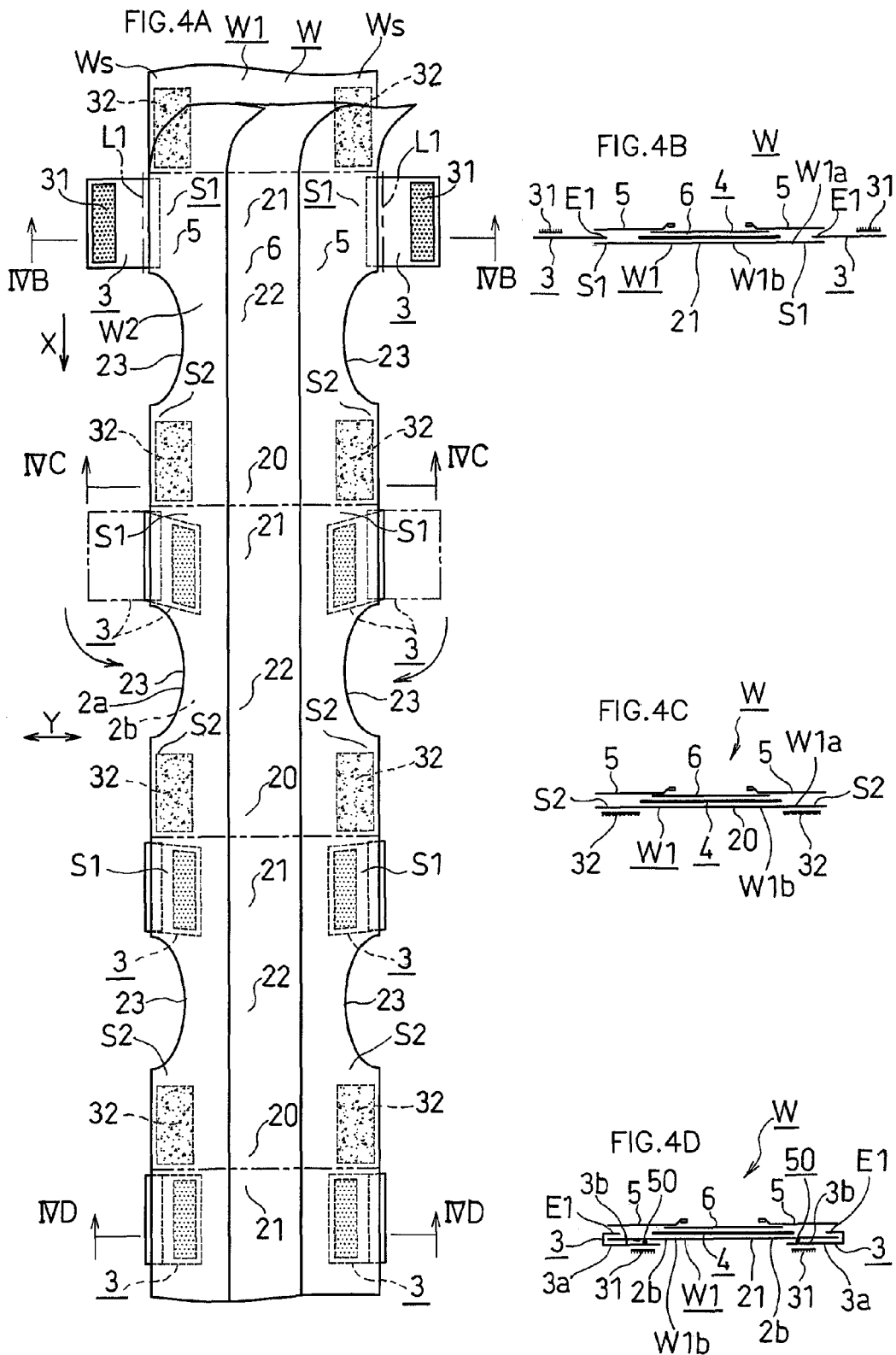

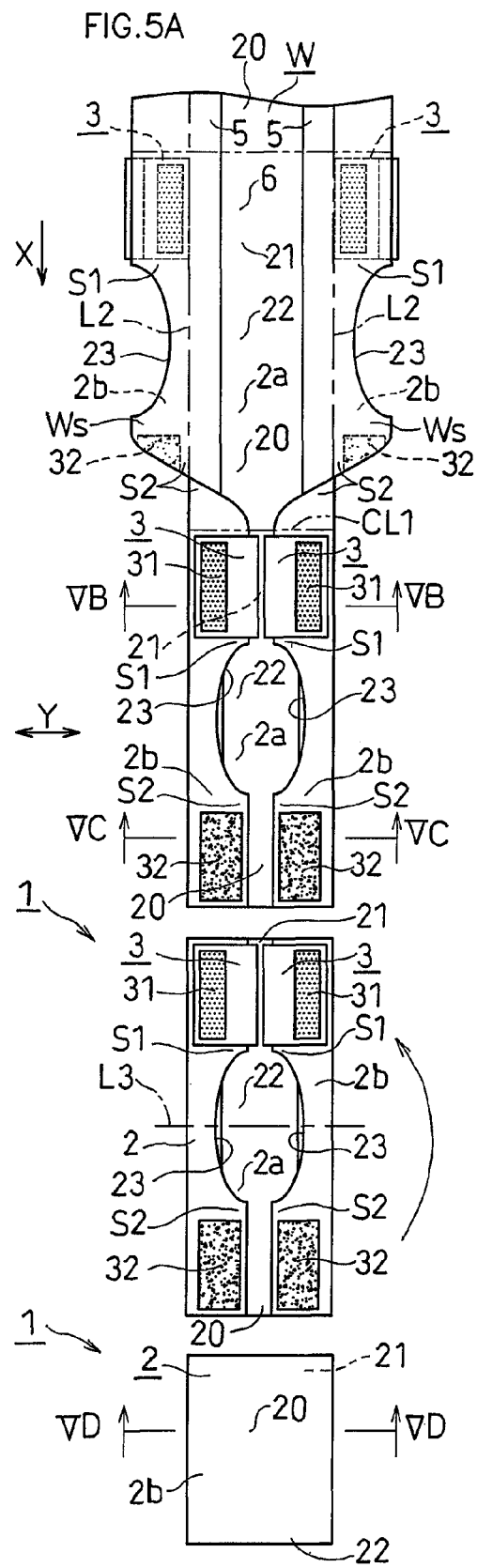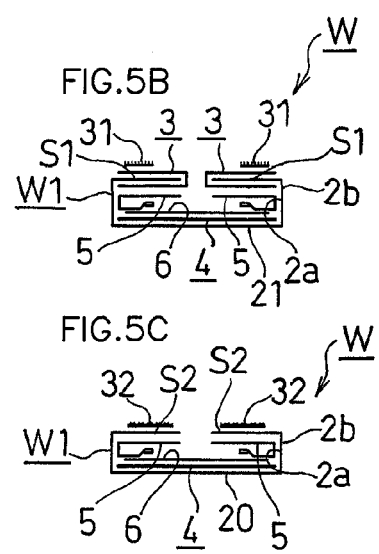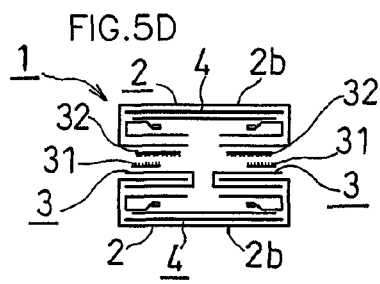

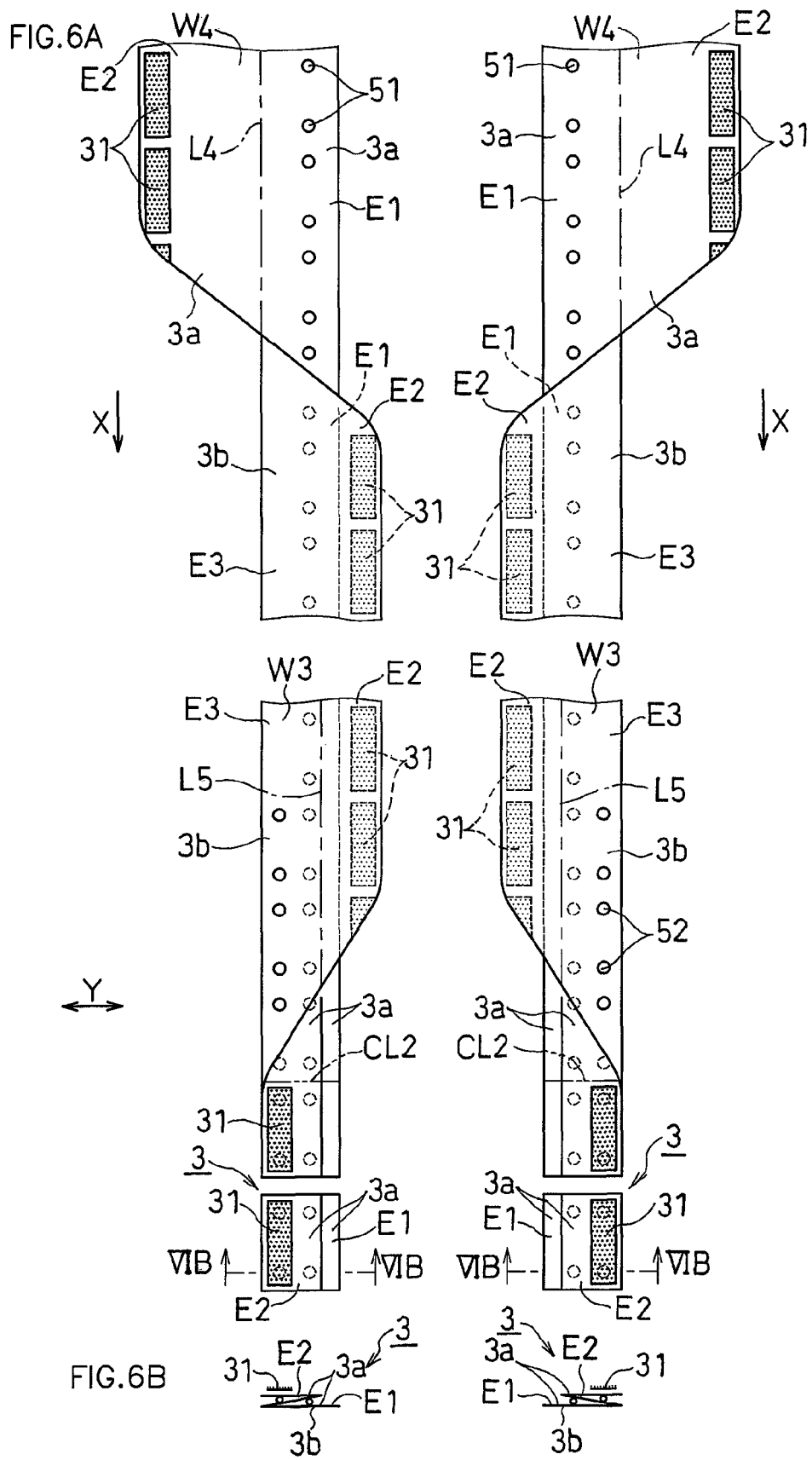

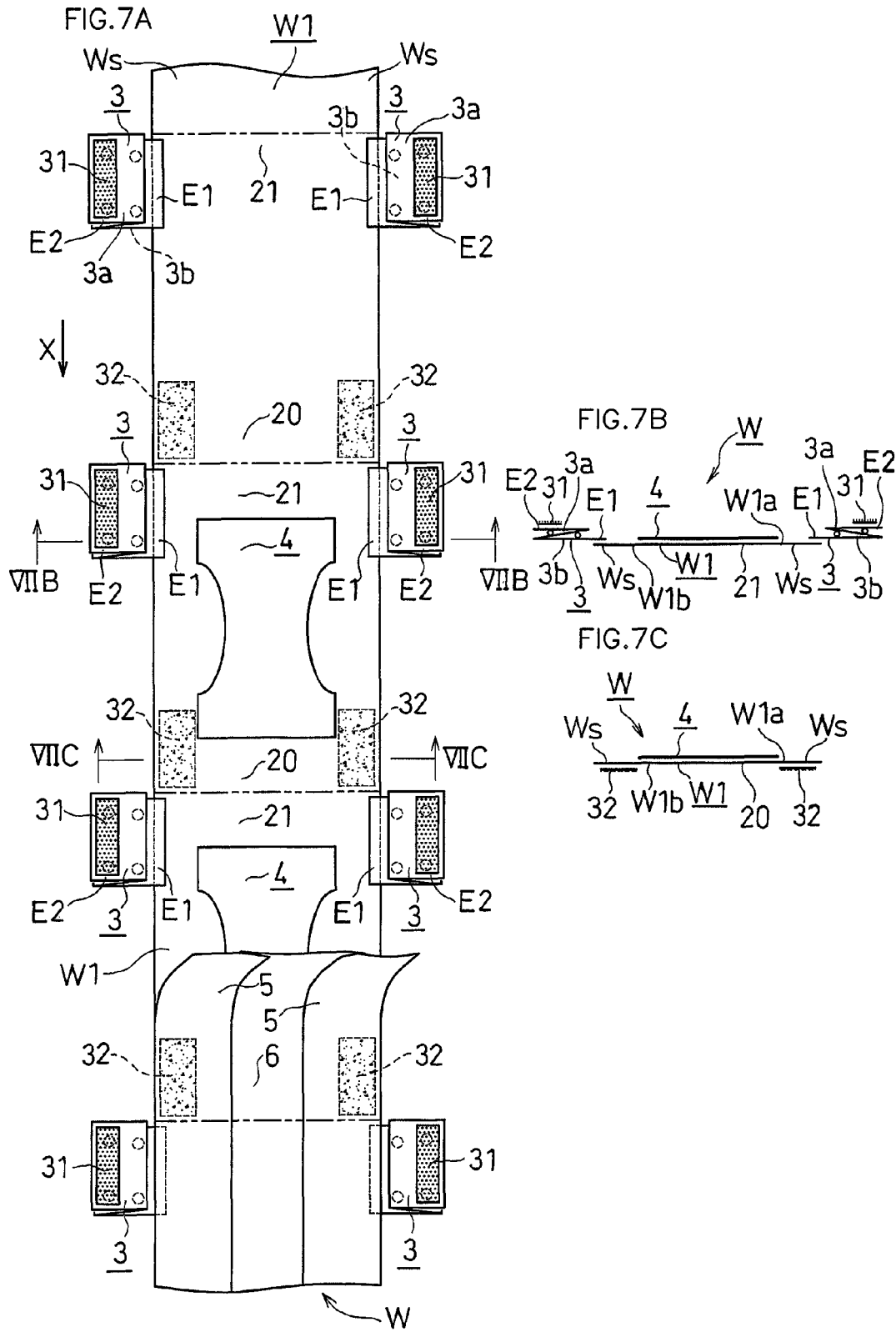

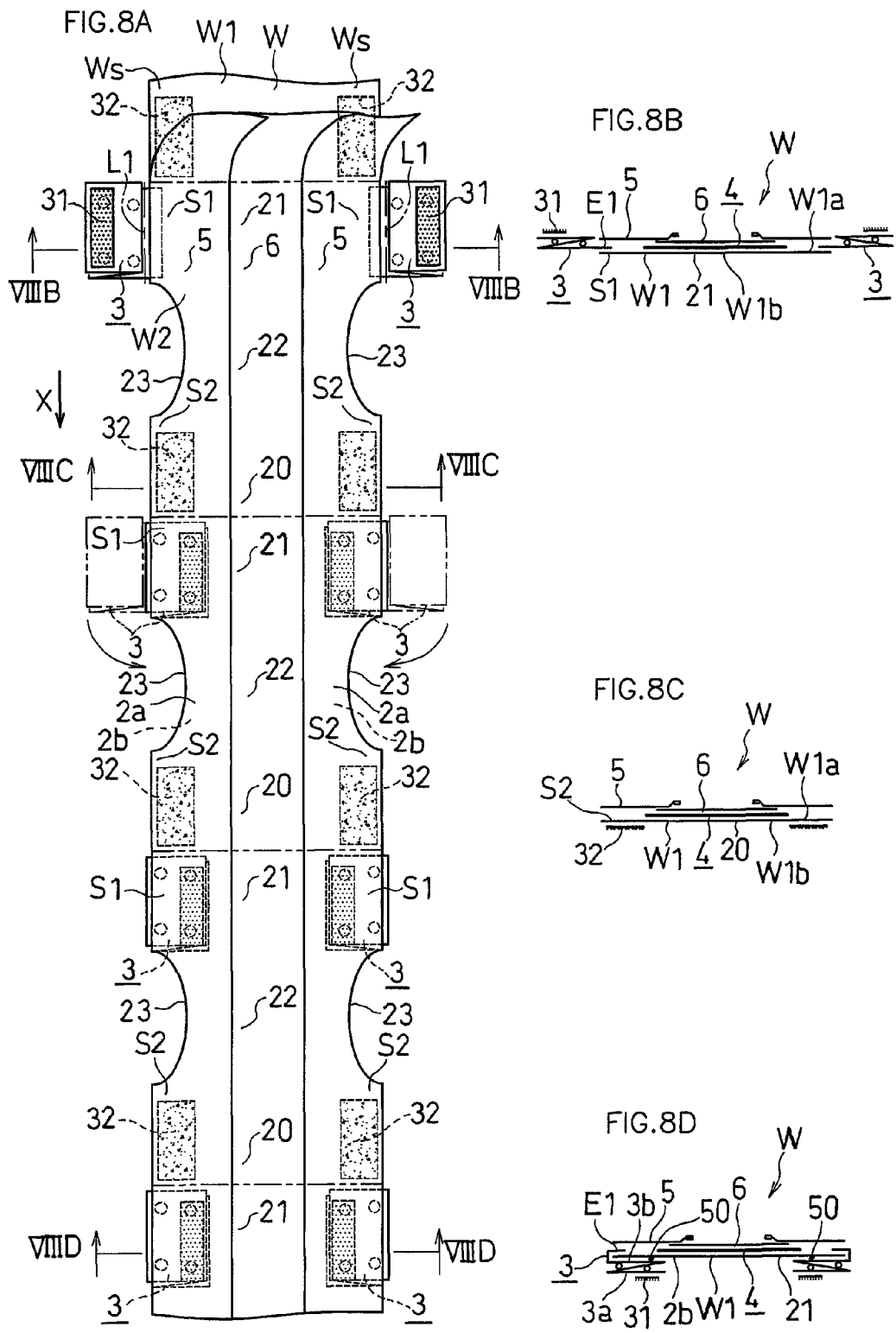

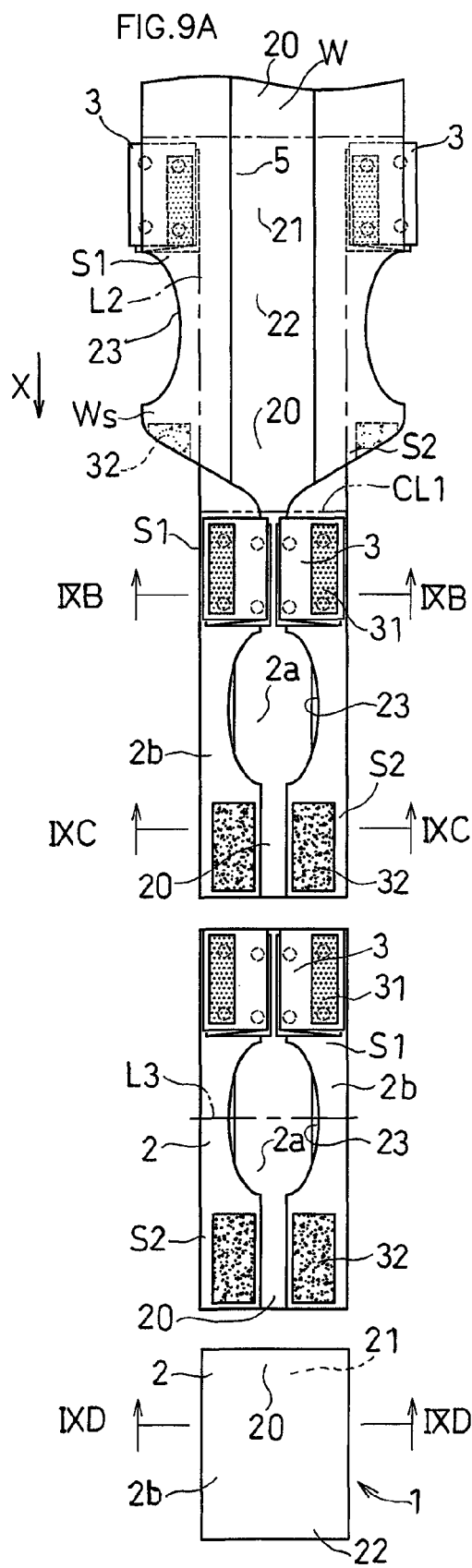
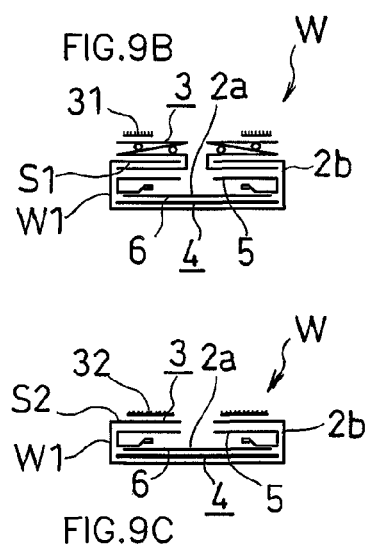
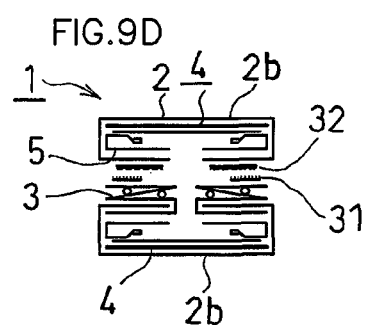

METHOD FOR MANUFACTURING DISPOSABLE WORN ARTICLE

TECHNICAL FIELD

The present invention relates to a method for manufacturing a disposable worn article.

BACKGROUND ART

The so-called "open-type diaper" which includes a diaper body and a girth portion provided on a side edge of one of the front side and the back side of the diaper body has been known in the art as a disposable worn article. The open-type diaper has an advantage that it can be used in the form of either a pants-type or a tape-type by fastening in advance the girth portion to the other one of the front side and the back side with a fastener. A method for fastening the girth portion of such a diaper to the diaper body with a fastener in advance so that it is provided as a pants-type has been proposed in the art (see the first patent document).

CITATION LIST

Patent Document

[FIRST PATENT DOCUMENT] Japanese National Phase PCT Laid-Open Publication No. 2002-518097 (Abstract)

SUMMARY OF THE INVENTION

Technical Problem

In the first patent document, a continuous member is cut into individual diapers, and then the girth portion is folded.

That is, in the first patent document, the girth portion is folded in a state where the continuous member has been cut into individual diapers. This results in a problem that it is difficult to handle the girth portion and to fold the girth portion.

It is therefore an object of the present invention to provide a method for easily fastening a girth portion of a disposable worn article formed by a so-called "open-type diaper" in advance with a fastener.

Solution to Problem

In order to achieve object set forth above, a method for manufacturing a disposable worn article of the present invention is a method for manufacturing a disposable worn article including: a back portion covering a back side of a wearer; a front portion covering a front side of the wearer; a crotch portion between the front portion and the back portion; a first side flap extending in a girth direction on each side of the back portion; a second side flap extending in the girth direction on each side of the front portion; a girth portion further extending in the girth direction from one of the first and second side flaps and lying on another one of the first and second side flaps when the worn article is worn; a first fastener member provided on a skin-contact surface of the girth portion; and a second fastener member provided on a non-skin-contact surface of the other one of the first and second side flaps and capable of engaging with the first fastener member, the method including: a carrying step of carrying a continuous member of a combined web forming the worn article in a direction perpendicular to the girth direction; a first folding step of folding the girth portion along a virtual first line extending in the perpendicular direction, while performing the carrying step, so that a non-skin-contact surface of the girth portion lies on a non-skin-contact surface of the one of the first and second side flaps; a second folding step of folding the first and second side flaps along a virtual second line extending in the perpendicular direction, while performing the carrying step and after the first folding step, so that skin-contact surfaces of the first and second side flaps lie on skin-contact surfaces of the back portion and the front portion, respectively; a cut-off (severing) step of cutting the continuous member into individual worn articles, after the second folding step; and a third folding step of folding the individual worn articles along a virtual third line extending in the girth direction so that the first fastener member provided on the skin-contact surface of the girth portion lies on the second fastener member provided on the non-skin-contact surface of the other one of the first and second side flaps.

Advantageous Effects of Invention

According to the present invention, since the girth portion is folded in the first folding step, prior to the cut-off step, the subsequent steps can be performed smoothly without being obstructed by the long girth portion extending in the girth direction.

Since the worn article is severed individually after the continuous member of the combined web is folded along the perpendicular line in the second folding step before the cut-off step, the second folding step can be performed continuously and with high precision.

Moreover, as the worn article is folded in the third folding step after the cut-off step so that the first fastener member lies on the second fastener member, the worn article can be folded in a compact manner, and as the first and second fastener members engage with each other, the girth portion is connected to the side of the other one of the first and second side flaps, thereby forming pants-type diapers in advance.

BRIEF DESCRIPTION OF THE DRAWINGS

FIGS. 3A and 3B are a plan view and a cross-sectional view, respectively, showing a manufacturing method of the embodiment.

FIG. 4A is a plan view showing the manufacturing method of the embodiment, and FIGS. 4B, 4C and 4D are cross-sectional views thereof.

FIG. 5A is a plan view showing the manufacturing method of the embodiment, and FIGS. 5B, 5C and 5D are cross-sectional views thereof.

FIGS. 6A and 6B are a plan view and a cross-sectional view, respectively, showing a process of manufacturing girth portions of Embodiment 2.

FIG. 7A is a plan view showing a manufacturing method of Embodiment 2, and FIGS. 7B and 7C are cross-sectional views thereof.

FIG. 8A is a plan view showing the manufacturing method of Embodiment 2, and FIGS. 8B, 8C and 8D are cross-sectional views thereof.

FIG. 9A is a plan view showing the manufacturing method of Embodiment 2, and FIGS. 9B, 9C and 9D are cross-sectional views thereof.

BEST MODE FOR CARRYING OUT THE INVENTION

In a preferred embodiment of the present invention, the method further includes a step of tentatively fastening the non-skin-contact surface of the girth portion to the non-skin-contact surface of the one of the first and second side flaps, simultaneously with the first folding step or after the first folding step.

In this embodiment, since the folded girth portions are tentatively fastened to the first or second side flap, the girth portions will not open inadvertently in subsequent steps. This further facilitates the handling of the girth portions.

In another preferred embodiment of the present invention, the method further includes: a fourth folding step of folding the girth portion along a virtual fourth line extending in the perpendicular direction so that skin-contact surfaces of the girth portion lie on each other; and a fifth folding step of folding the girth portion along a virtual fifth line extending in the perpendicular direction so that non-skin-contact surfaces of the girth portion lie on each other.

In this embodiment, by further performing the fourth and fifth folding steps, even girth portions that are long in the girth direction can be fastened to the diaper body.

Embodiment 1

An embodiment of the present invention will now be described with reference to the drawings.

FIGS. 1 to 5D show Embodiment 1.

Figure 1:
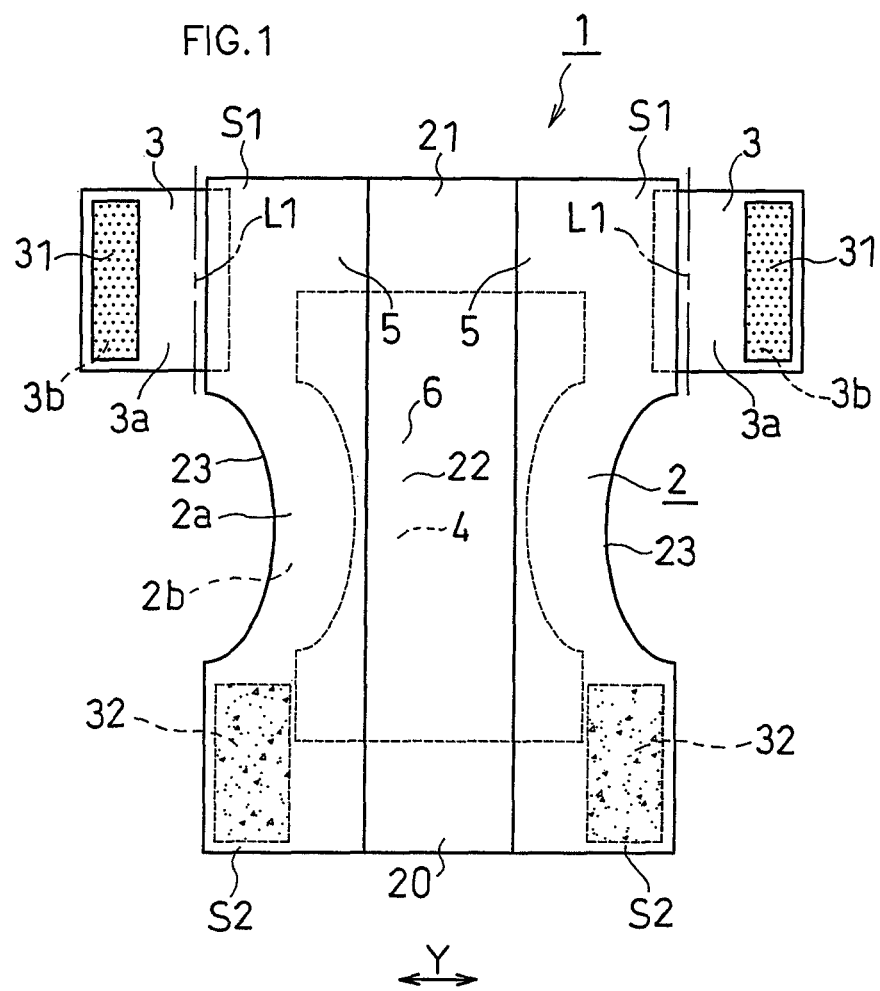
FIG. 1 is a schematic front view showing a diaper of Embodiment 1 of the present invention in an open state.

Diaper 1:

FIG. 1 is a plan view showing, in an unfolded state, a diaper 1 manufactured folded by a manufacturing method of Embodiment 1.

As shown in FIG. 1, the diaper 1 includes a diaper body 2, and a pair of girth portions 3. The diaper body 2 includes a front portion 20 covering the front side of the wearer, a back portion 21 covering the back side of the wearer, and a crotch portion 22 between the front portion 20 and the back portion 21. An absorbent body 4 is provided on the diaper body 2.

First side flaps S1 extending in the girth direction Y are formed integral with the diaper body 2, on opposite sides of the back portion 21 in the girth direction Y. Second side flaps S2 extending in the girth direction Y are formed integral with the diaper body 2, on opposite sides of the front portion 20 in the girth direction Y.

The girth portions 3 and 3 are provided on the first side flaps S1 each protruding from the first side flap S1 in the girth direction. The girth portion 3 further extends in the girth direction Y from the first side flap S1. When worn, the girth portion 3 lies on a non-skin-contact surface 2b of the second side flap S2 shown in FIG. 2. Note that the girth portions 3 and 3 may have elasticity in the girth direction Y, etc.

A first fastener member 31 formed by a male touch fastener, for example, is provided on a skin-contact surface 3a of the girth portion 3 of FIG. 1. On the other hand, a second fastener member 32 formed by a female touch fastener, for example, is provided on the non-skin-contact surface 2b of the second side flap S2. Note that where the non-skin-contact surface 2b of the diaper body 2 is formed by a non-woven fabric, the second fastener member may be formed by the non-woven fabric.

The diaper body 2 may include a top sheet 6 covering the absorbent body 4, and a pair of three-dimensional gathers 5.

The diaper body 2 may include around-leg portions (leg holes) 23 which are cut so as to conform to the legs of the wearer, and the around-leg portions 23 may include elastic members formed by rubber threads, or the like, for example, so as to conform to the legs of the wearer.

Moreover, an elastic member for fitting the diaper 1 to the wearer may be provided in the front portion 20 and the back portion 21 of the diaper body 2. The elastic member may be, for example, a plurality of rubber threads or rubber tapes, a material including a film or a thermoplastic resin, or the like.

After the girth portion 3 is folded along a virtual first line L1 (FIG. 4A) toward the side of the non-skin-contact surface 2b of the diaper body 2, the side flaps are folded along a virtual second line L2 so that skin-contact surfaces 2a of the diaper body 2 face each other as shown in FIG. 5A. Moreover, the diaper body 2 is folded along a virtual third line L3 shown in FIG. 2. As the diaper 1 is folded along the virtual third line L3, the first fastener member 31 of the girth portion 3 and the second fastener member 32 provided on the second side flap S2 engage with each other, and the front portion 20 side of the diaper body 2 and the back portion 21 side thereof are fastened with each other.

Note that the second line L2 of FIG. 5 is generally parallel to the first line L1 of FIG. 1.

Next, a method for manufacturing the diaper 1 will be described.

Step of Carrying Continuous Member W of Combined Web:

As shown in FIGS. 3A to 5A, the continuous member W of the combined web forming the diaper 1 is carried in a direction (longitudinal direction) X perpendicular to the girth direction Y. The continuous member W is obtained by layering or joining (fastening) the girth portion 3, the second fastener member 32, the absorbent body 4, the three-dimensional gathers 5, the top sheet 6, etc., on/to a continuous sheet W1 made of a liquid-impermeable resin film or a non-woven fabric, for example.

Fastening Girth Portion 3:

As shown in FIG. 3A, the girth portions 3 are joined (fastened) to the opposite end portions Ws of the continuous sheet W1 made of a non-woven fabric, or the like, for example. Pairs of girth portions 3 are fastened intermittently in the longitudinal direction X. First end portions E1 of the girth portions 3 in the girth direction Y are fastened to the opposite end portions Ws. The first fastener members 31 which are male touch fasteners, for example, are provided on the skin-contact surfaces 3a of second end portions E2 of the girth portions 3.

Note that the joining (fastening) may be thermal welding or sonic (ultrasonic bonding) welding or bonding with an adhesive such as a hot-melt resin.

Fastening Second Fastener Member 32:

On the other hand, a pair of second fastener members 32 which are female touch fasteners, for example, is fastened to a non-skin-contact surface W1b of the continuous sheet W1. The second fastener members 32 are also joined (fastened) intermittently in the longitudinal direction X.

Fastening Absorbent Body 4:

Then, the absorbent body 4 is placed generally at the center of a skin-contact surface W1a of the continuous sheet W1 in the girth direction Y. The absorbent bodies 4 are placed intermittently in the longitudinal direction X.

Thus, as shown in FIG. 3B, the first end portions E1 of the girth portions 3 are joined (fastened) to the opposite end portions Ws of the skin-contact surface W1a of the continuous sheet W1 to be the back portion 21. On the other hand, as shown in FIG. 3C, the second fastener members 32 are joined (fastened) to the opposite end portions Ws of the non-skin-contact surface W1b of the continuous sheet W1 to be the front portion 20.

Then, as shown in FIG. 3A or 4A, the three-dimensional gathers 5 and the top sheet 6 are placed on the continuous sheet W1 so as to cover the absorbent body 4, thereby producing the continuous member W of the combined web.

Therefore, as shown in FIG. 4B, the continuous member W to be later severed (cut) into the diaper bodies 2 includes the absorbent body 4 placed on the skin-contact surface W1a of the continuous sheet W1, and further includes the three-dimensional gathers 5 and the top sheet 6 placed thereon, in a lateral cross section of the back portion 21. On the other hand, as shown in FIG. 4C, the continuous member W includes the absorbent body 4 placed on the skin-contact surface W1a of the continuous sheet W1, and further includes the three-dimensional gathers 5 and the top sheet 6 placed thereon, in a lateral cross section of the front portion 20.

After the continuous member W of the combined web is produced, portions of the continuous member W to be the around-leg portions 23 are removed at predetermined intervals as shown in FIG. 4A. With this removal, the continuous member W includes the first side flaps S1 formed extending in the girth direction Y on opposite sides of the back portion 21, and includes the second side flaps S2 formed extending in the girth direction Y on opposite sides of the front portion 20.

First Folding Step:

Then, as shown in FIG. 4A, the girth portion 3 is folded along the virtual first line L1 extending in the longitudinal direction X of the girth portion 3 during the carrying step. Thus, as shown in FIG. 4D, a non-skin-contact surface 3b of the girth portion 3 lies so as to face the non-skin-contact surface 2b of the back portion 21.

That is, by the first folding step, the girth portion 3 is folded so that the non-skin-contact surface 3b of the girth portion 3 comes into contact with the non-skin-contact surface W1b of the continuous sheet W1 as shown in FIG. 4D. Note that the girth portion 3 may be tentatively fastened to the continuous sheet W1 by an adhesive 50, or the like, for example. The tentative fastening may be thermal welding, or the like.

Second Folding Step:

After the first folding step, the skin-contact surfaces 2a of the first and second side flaps S1 and S2 are folded so as to face the skin-contact surfaces 2a of the back portion 21 and the front portion 20 during the carrying step, as shown in FIG. 5A. This folding is done along the virtual second line L2 extending in the longitudinal direction X.

By the second folding step, the skin-contact surface 2a of the first side flap S1 faces the skin-contact surface 2a of the back portion 21 as shown in FIG. 5B, and the skin-contact surface 2a of the second side flap S2 faces the skin-contact surface 2a of the front portion 20 as shown in FIG. 5C.

Figure 2:
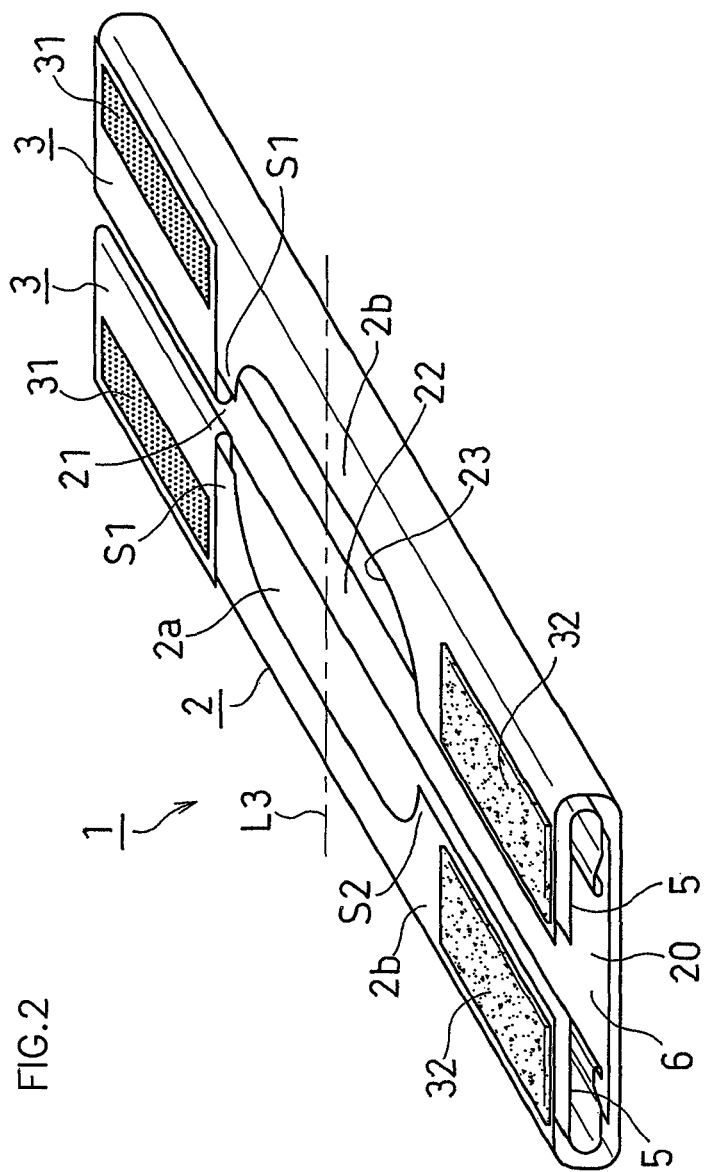
FIG. 2 is a schematic perspective view of a worn article having been cut into an individual diaper in the cut-off step of the embodiment.

Sever (Cut-Off) Step:

After the second folding step, the continuous member W is severed (cut) along a first cut line CL1 extending in the girth direction Y as shown in FIG. 5A into individual diapers 1 as shown in FIG. 2.

Third Folding Step:

Then, as shown in FIG. 5A, the diaper 1 is folded along the virtual third line L3 extending in the girth direction Y. That is, the diaper 1 is folded as shown in FIG. 5D so that the first fastener member 31 provided on the skin-contact surface 3a of the girth portion 3 lies on the second fastener member 32 provided on the non-skin-contact surface 2b of the second side flap S2.

Therefore, the third line L3 is set generally at the center of the diaper 1 in the longitudinal direction X.

Embodiment 2

FIGS. 6A to 10B show Embodiment 2.

In Embodiment 2, as shown in FIGS. 6A and 6B, the girth portion 3 which has been folded a plurality of times is joined (fastened) to the continuous sheet W1 (FIG. 7A). What is different from Embodiment 1 described above will be mainly described in the following description.

Girth Portion 3:

As shown in FIG. 6B, the pair of girth portions 3 are symmetrically folded in a Z-letter shape or an inverse Z-letter shape. The first end portions E1 of the girth portions 3 are portions to be fastened to the opposite end portions Ws of the continuous sheet W1 of FIG. 7A, and the first fastener members 31 are fastened to the skin-contact surfaces 3a of the other, second end portions E2 of the girth portions 3.

Next, a method for manufacturing the girth portion 3 will be described.

Step of Carrying Girth Portion 3:

As shown in FIG. 6A, continuous webs W4 to be the pair of girth portions 3 are carried in a direction (longitudinal direction) X perpendicular to the girth direction Y. The first fastener members 31 are placed and joined (fastened) at predetermined intervals on the second end portions E2 of the continuous webs W4.

Fourth Folding Step:

An adhesive 51 is applied intermittently on the skin-contact surface 3a while carrying the continuous webs W4, and the continuous webs W4 are folded along virtual fourth lines L4 extending in the longitudinal direction X so that the skin-contact surfaces 3a to be the girth portions 3 face each other after the application. The skin-contact surfaces 3a brought into contact with each other by the folding are tentatively joined (fastened) to each other by the adhesive 51, for example. The tentative joint (fastening) may be thermal welding, or the like.

Note that the fourth lines L4 are generally parallel to the first lines L1.

By the folding, the second end portions E2 of the continuous webs W4 are folded so as to cover the first end portions E1 and to protrude further in the inward direction (toward the first end portions E1) past the first end portions E1. That is, the fourth lines L4 are set so that the first fastener members 31 on the side of the skin-contact surfaces 3a of the second end portions E2 do not come into contact with the skin-contact surfaces 3a of the first end portions E1.

By such folding, third end portions E3 are formed at end portions opposite to the second end portions E2 in the girth direction Y.

Fifth Folding Step:

Then, an adhesive 52 is applied intermittently on the non-skin-contact surfaces 3b while carrying the continuous webs W4, and the continuous webs W4 are folded along virtual fifth lines L5 extending in the longitudinal direction X so that the non-skin-contact surfaces 3b face each other after the application. That is, the second end portions E2 are folded back toward the third end portions E3. By such folding back, the non-skin-contact surfaces 3b of the second end portions E2 of the continuous webs W4 face the non-skin-contact surfaces 3b of the third end portions E3. The non-skin-contact surfaces 3b brought into contact with each other by such folding back are tentatively joined (fastened) to each other by the adhesive 52. The tentative joint (fastening) may be thermal welding, or the like.

Note that the fifth lines L5 are parallel to the first lines L1 and the fourth lines L4.

Step of Severing (Cutting Off) Girth Portions 3:

After the fifth folding step, the continuous webs W4 are severed (cut) along a second cut line CL2 extending in the girth direction Y into individual girth portions 3, thereby producing the girth portions 3.

With the girth portions 3 thus produced, the first end portions E1 of the girth portions 3 of FIG. 7A are joined (fastened) to the opposite end portions Ws of the continuous sheet W1 as in Embodiment 1 described above.

Note that the manufacturing method thereafter of Embodiment 2 is similar to that of Embodiment 1 and will not be described below.

Figure 10A:
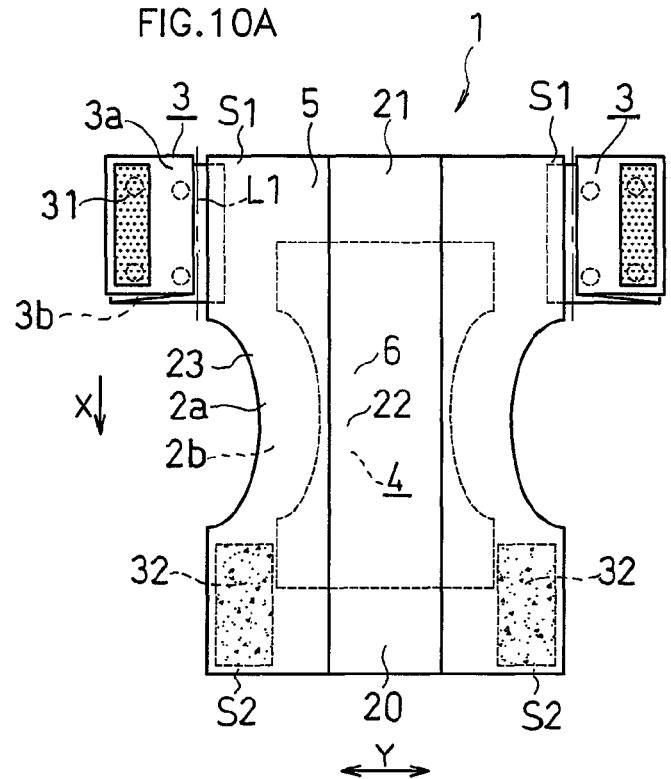
FIG. 10A is a schematic front view showing a diaper of Embodiment 2 in a state where the girth portions of the diaper are folded.

Also in Embodiment 2, the diaper 1 is folded as shown in FIGS. 9A and 9D. FIG. 10A shows the diaper 1 in an open state. Moreover, FIG. 10B shows the diaper 1 in which the Z-folded girth portions 3 are stretched out.

Figure 10B:
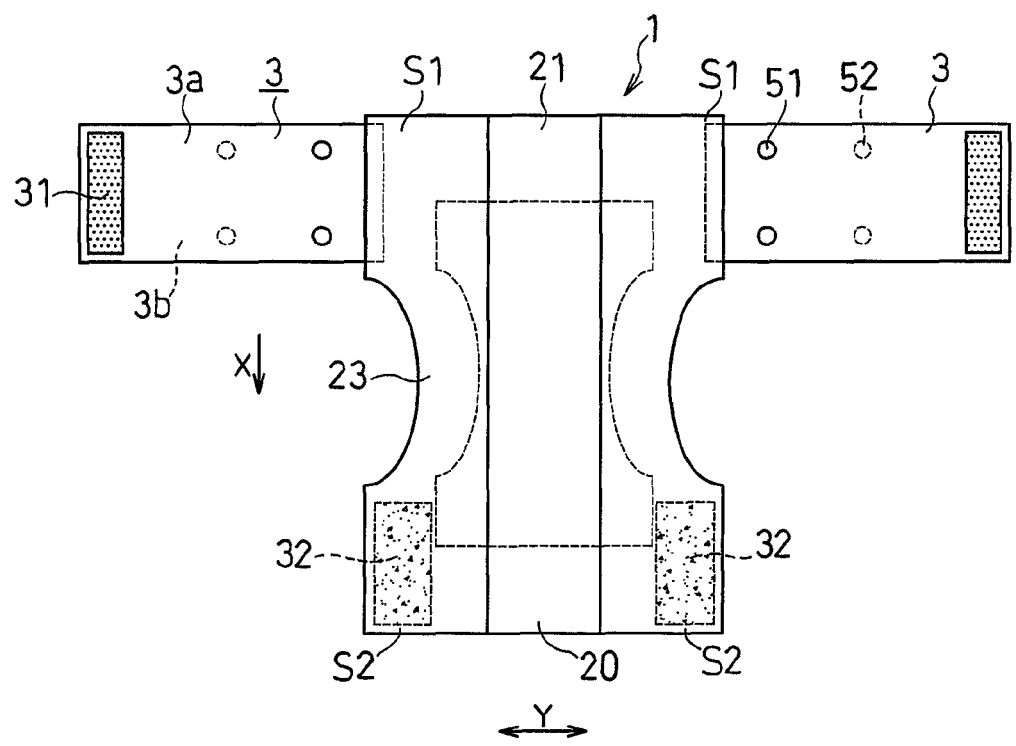
FIG. 10B is a schematic front view showing the diaper in an open state.

As can be seen from FIG. 10B, long girth portions 3 can be employed in Embodiment 2. This is because the girth portions 3 are not obstructive during the second folding step since the girth portions 3 are Z-folded before the second folding step of FIG. 9A.

Note that although the above embodiments each illustrate a diaper 1 including a diaper body 2 and girth portions 3 separate from the diaper body 2, the diaper may include the diaper body 2 and the girth portions 3 formed integral with each other.

While preferred embodiments have been described above with reference to the drawings, obvious variations and modifications will readily occur to those skilled in the art upon reading the present specification.

For example, the girth portion may be joined (fastened) to the second side flaps on the front side of the diaper body.

In a case where the girth portions are folded a plurality of times, the girth portions may be folded a plurality of times after the girth portions are joined (fastened) to the continuous member of the diaper body.

Thus, such variations and modifications shall fall within the scope of the present invention as defined by the appended claims.

INDUSTRIAL APPLICABILITY

The present invention is applicable to methods for manufacturing diapers and manufacturing apparatuses therefor.

DESCRIPTION OF THE REFERENCE NUMERALS

1: Diaper (an example of a disposable worn article)
2: Diaper body
2a: Skin-contact surface
3: Girth portion
3a: Skin-contact surface
3b: Non-skin-contact surface
31: First fastener member
32: Second fastener member
L1: First line
L2: Second line
L3: Third line
L4: Fourth line
L5: Fifth line
S1: First side flap
S2: Second side flap
X: Longitudinal direction
Y: Girth direction

The invention claimed is:

1. A method for manufacturing a disposable worn article including: a back portion covering a back side of a wearer; a front portion covering a front side of the wearer; a crotch portion between the front portion and the back portion; a first side flap extending in a girth direction on each side of the back portion; a second side flap extending in the girth direction on each side of the front portion; respective girth portions joined to each of the first side flaps or each of the second side flaps and lying on the other one of the first and second side flaps when the worn article is worn, the girth portions further extending in the girth direction beyond respective side edges of the first and second side flaps in the girth direction; respective first fastener members provided on a skin-contact surface of each of the girth portions; and respective second fastener members provided on a non-skin-contact surface of each of the other one of the first and second side flaps and capable of engaging with a corresponding one of the first fastener members, the method comprising:

a carrying step of carrying a continuous member of a combined web forming the worn article in a direction perpendicular to the girth direction;

a first folding step of folding the girth portions along a virtual first line extending in the perpendicular direction, while performing the carrying step, so that a non-skin-contact surface of the girth portions lies on a non-skin-contact surface of the one of the first and second side flaps;

a second folding step of folding the first and second side flaps along a virtual second line extending in the perpendicular direction, while performing the carrying step and after the first folding step, so that a skin-contact surface of the first side flap lies on a skin-contact surface of the back portion and a skin-contact surface of the second side flap lies on a skin-contact surface of the front portion;

a severing step of severing an individual worn article from the continuous member after the second folding step; and a third folding step of folding the individual worn article along a virtual third line extending in the girth direction so that one of the first fastener members provided on the skin-contact surface of one of the girth portions lies on one of the second fastener members provided on the non-skin-contact surface of the other one of the first and second side flaps, and another one of the first fastener members provided on the skin-contact surface of the other one of the girth portions lies on another one of the second fastener members provided on the non-skin-contact surface of the other one of the first and second side flaps.

2. The method for manufacturing a disposable worn article according to claim 1, a member forming the respective girth portions is different from a member forming the first side flap and the second side flap.

3. The method for manufacturing a disposable worn article according to claim 2, further comprising a step of tentatively fastening the non-skin-contact surface of the respective girth portions to the non-skin-contact surface of the one of the first and second side flaps, simultaneously with the first folding step or after the first folding step.

4. The method for manufacturing a disposable worn article according to claim 2, further comprising:

a fourth folding step of folding the girth portions along a virtual fourth line extending in the perpendicular direction so that skin-contact surfaces of the girth portions lie on each other; and a fifth folding step of folding the girth portions along a virtual fifth line extending in the perpendicular direction so that non-skin-contact surfaces of the girth portions lie on each other.

5. The method for manufacturing a disposable worn article according to claim 2, the respective girth portions are joined to only one of the first side flap and the second side flap.

\* \* \* \* \*